United States Patent [19]

Sircar et al.

[11] Patent Number: 4,734,415

[45] Date of Patent: * Mar. 29, 1988

[54] SUBSTITUTED 4,5-DIHYDRO-6-(SUBSTITUTED)-PHENYL-3(2H)-PYRIDAZINONES AND 6-(SUBSTITUTED)PHENYL-3(2H)-PYRIDAZINONES

[75] Inventors: Ila Sircar; James A. Bristol, both of Ann Arbor, Mich.

[73] Assignee: Warner-Lambert Company, Morris Plains, N.J.

[*] Notice: The portion of the term of this patent subsequent to Oct. 12, 1999 has been disclaimed.

[21] Appl. No.: 477,695

[22] Filed: Mar. 22, 1983

Related U.S. Application Data

[63] Continuation-in-part of Ser. No. 407,973, Aug. 13, 1982, which is a continuation-in-part of Ser. No. 402,488, Jul. 27, 1982, which is a continuation-in-part of Ser. No. 302,181, Sep. 17, 1981, Pat. No. 4,353,905.

[51] Int. Cl.$^4$ .................... C07D 237/04; A61K 31/50
[52] U.S. Cl. .................... 514/247; 514/252; 544/238; 544/239
[58] Field of Search ............... 544/238, 239; 514/247, 514/252

[56] References Cited

U.S. PATENT DOCUMENTS

| 3,975,388 | 8/1976 | Hakim et al. | 544/238 |
| 4,361,563 | 11/1982 | Austel et al. | 544/239 |
| 4,353,905 | 10/1982 | Sircar et al. | 424/250 |
| 4,397,854 | 8/1983 | Sircar | 544/239 |
| 4,507,298 | 3/1985 | Lautenschläger | 514/247 |
| 4,521,415 | 6/1985 | Katakami et al. | 514/252 |
| 4,551,455 | 11/1985 | Hilboll et al. | 544/238 |

FOREIGN PATENT DOCUMENTS

| 0059688 | 2/1982 | European Pat. Off. |
| 2157453 | 11/1971 | Fed. Rep. of Germany |

*Primary Examiner*—Nicholas S. Rizzo
*Attorney, Agent, or Firm*—Roland A. Daignault

[57] ABSTRACT

Substituted 4,5-dihydro-6-(substituted)phenyl-3(2H)-pyridazinone compounds and 6-(substituted)phenyl-3(2H)-pyridazinone compounds and pharmaceutically acceptable salts thereof are useful as cardiotonic and antihypertensive agents.

Said compounds cause a significant increase in myocardial contractility in the dog. Said compounds also cause a decrease in blood pressure in the spontaneously hypertensive rat. Said compounds are produced by reacting substituted γ-oxobenzenebutanoic acids with suitably substituted hydrazines to provide 4,5-dihydro-6-(substituted)phenyl-3(2H)-pyridazinones which are dehydrogenated to 6-(substituted)phenyl-3(2H)-pyridazinones.

Both the intermediate 4,5-dihydro-6-(substituted)phenyl-3(2H)-pyridazinones and the 6-(substituted)phenyl-3(2H)-pyridazinones are useful as cardiotonic and antihypertensive agents.

34 Claims, No Drawings

SUBSTITUTED 4,5-DIHYDRO-6-(SUBSTITUTED)-PHENYL-3(2H)-PYRIDAZINONES AND 6-(SUBSTITUTED) PHENYL-3(2H)-PYRIDAZINONES

CROSS-REFERENCE TO RELATED APPLICATIONS

This is a continuation-in-part application of copending U.S. patent application Ser. No. 407,973, filed Aug. 13, 1982, which is a continuation-in-part of copending U.S. patent application Ser. No. 402,488 filed July 27, 1982, which is a continuation-in-part application of U.S. patent application Ser. No. 302,181, filed Sept. 17, 1981, now U.S. Pat. No. 4,353,905.

BACKGROUND OF THE INVENTION 4,5-Dihydro-6(1H)-pyridazinone derivatives having cardiovascular and antiinflammatory activity have been described in German Offenlegungsschrift No. 2,157,453.

Morpholino-phenyl-pyridazinone derivatives as antithrombotic agents have been described in European Patent Publication No. 0 059 688.

The present invention relates to 4,5-dihydro-6-(substituted)phenyl-3(2H)-pyridazinone compounds and 6-(substituted)phenyl-3(2H)-pyridazinone compounds useful as cardiotonic agents. The present invention also relates to the above mentioned pyridazinone compounds useful as antihypertensive agents.

SUMMARY OF THE INVENTION

The present invention relates to novel substituted 4,5-dihydro-6-(substituted)phenyl-3(2H)-pyridazinone compounds and 6-(substituted)phenyl-3(2H)-pyridazinone compounds useful as cardiotonic agents having the structural formula (I):

[Structure I]

wherein ===== represents a double or single bond between two carbon atoms; Q is oxygen or sulfur; $R_2$ is hydrogen or lower alkyl; $R_3$ is hydrogen, lower alkyl, or when ===== represents a single bond, $R_3$ is di-lower alkyl; $R_4$ is hydrogen, lower alkyl, or when ===== represents a double bond, $R_4$ is hydrogen, lower alkyl, amino, cyano, $CONR_aR_b$, hydroxy, $CH_2OH$, or $$\overset{(O)_n}{\underset{S-R_c,}{\|}}$$

where $R_a$ and $R_b$ are independently H or lower alkyl, $R_c$ is lower alkyl or phenyl, and n is zero to two; or $R_3$ and $R_4$ taken together form a ring containing 1 to 4 carbon atoms; Y is H, halogen, lower alkyl, lower alkoxy, or a group such as $$O-CH_2-\underset{OH}{\overset{|}{C}H}-CH_2-NR_dR_e$$

where $R_d$ and $R_e$ are independently H, lower alkyl, straight or branched, $(CH_2)_n-R_f$ where $R_f$ is a benzene ring optionally substituted by halogen, hydroxy, lower alkyl, lower alkoxy, and $CF_3$ and n is zero to three, and A is any of the groups from a–e and is attached to the 3- or 4-position of the phenyl ring:

a.

$$A = \underset{R}{\overset{R'}{N}}\underset{R_1}{\overset{}{\diagdown}}N-X-$$

wherein $R_1$, R', and R are independently hydrogen or lower alkyl, $CH_2OH$, $SCH_3$, $SOCH_3$, $SO_2CH_3$, hydroxyalkyl, halogen, $(CH_2)_kNR''R'''$ wherein k is zero to two and R'' and R''' are independently hydrogen or lower alkyl, wherein lower alkyl contains one to six carbon atoms; or when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkoxy, and (iii) pyridine ring; X is a bond, or $O(CH_2)_n$ wherein n is two to five;

b.

$$A = L\underset{W}{\overset{Z}{\diagup}}N-X$$

wherein
(i) L=W=Z=CH
(ii) W=Z=N and L=CH or
(iii) L=Z=N and W=CH and X is a bond, $(CH_2)_n$ or $O(CH_2)_{n+1}$ wherein n is 1-4;

c.

$$A = i \quad R_5 \overset{\diagup\phantom{X}\diagdown}{\underset{\diagdown\phantom{X}\diagup}{\phantom{X}}} N-X$$

where $R_5$ is $CH_2$, O, S, $NR_6$ wherein $R_6$ is hydrogen, lower alkyl, $COR_7$ where $R_7$ is a benzene ring optionally substituted by halogen, lower alkyl, hydroxy, lower alkoxy, and $CF_3$ or $(CH_2)_nR_7$ where n is zero to four and $R_7$ is the same as defined above, with the proviso that when X is a bond and is attached to the 4-position of the benzene ring and Y is H, at least one of $R_2$, $R_3$ or $R_4$ must be lower alkyl, or (ii)

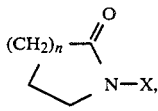

wherein n is one to three, or (iii)

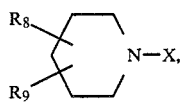

wherein $R_8$ and $R_9$ are independently hydrogen, lower alkyl, aryl, hydroxy, lower alkoxy, $NHR_{17}$ where $R_{17}$ is hydrogen, lower alkyl or lower alkanoyl, $CO_2R_{18}$ where $R_{18}$ is hydrogen or lower alkyl, $OCOBR_{10}$ where $R_{10}$ is lower alkyl, phenyl, or phenyl substituted by halo, lower alkyl, lower alkoxy, or trifluoromethyl, and B is a direct bond or NH; or taken together are carbonyl or ethylenedioxy and the pharmaceutically acceptable salts thereof; in all instances, X is the same as defined in 1b;

d.

wherein ----- represents a double or single bond between two carbon atoms; $R_{11}$ is hydrogen or lower alkyl; M is NH, O, or S, and X is either a direct bond or NH

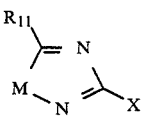

or where X, M, and $R_{11}$ are the same as defined above; or e. $NHPR_{12}R_{13}$ wherein P is a bond or carbonyl; $R_{12}$ is lower alkyl, straight or branched; $R_{13}$ is $NR_{14}R_{15}$ wherein $R_{14}$ and $R_{15}$ are individually hydrogen, lower alkyl, straight or branched, or taken together to form a 5-, 6-, or 7-membered ring or a group as defined in 1(a–c); or $S(O)_nR_{16}$ where n is zero to two and $R_{16}$ is lower alkyl, straight or branched, phenyl and the pharmaceutically acceptable salts thereof.

DETAILED DESCRIPTION

The compounds of formula I where $R_2$ is hydrogen may exist in tautomeric forms, for example, 6-[4-1H-imidazol-1-yl)phenyl]-3-(2H)-pyridazinones and/or 6-[4-(1H-imidazol-1-yl)phenyl]-3-pyridazinols of formula IA, illustrated as follows.

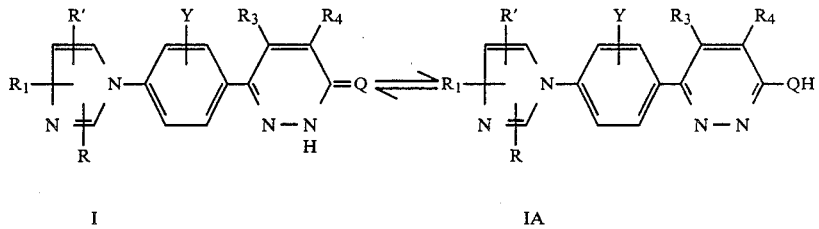

I    IA

The present invention also relates to 4,5-dihydro-6-(substituted)phenyl-3-(2H)-pyridazinones having the structural formula II.

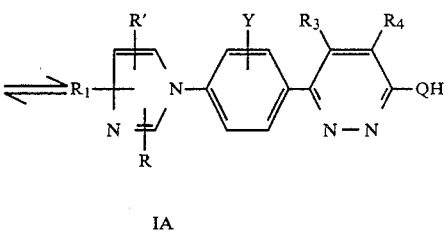

wherein A, Y, $R_2$, and $R_3$ are the same as defined above in the structural formula I, and $R_3$ is also di-lower alkyl.

These compounds are not only useful as intermediates for preparing the compounds of formula I, but are also useful as cardiotonic agents.

Another aspect of the present invention is a compound of the formula

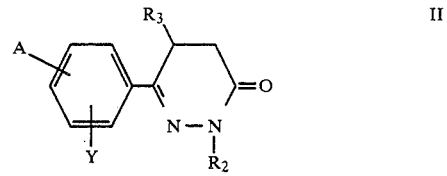

wherein $R_1$, R', X, $R_2$, and $R_3$ are defined above and pharmaceutically acceptable salts thereof.

Another aspect of the present invention is a compound of the formula

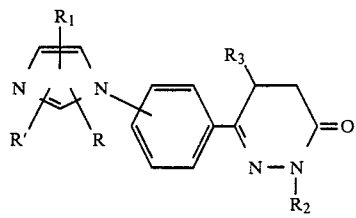

wherein $R_1$, R', R, $R_2$, and $R_3$ are as defined above and the pharmaceutically acceptable salts thereof.

Another aspect of the invention is a compound of the formula

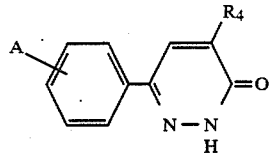

wherein $R_4$ and A have been defined in sections (a) and (b) above. Preferable groups for A are imidazole or imidazole substituted by lower alkyl, S-lower alkyl, or $CH_2OH$; tetrahydrobenzimidazole, benzimidazole, or 1,2,4-triazole. When A is as defined in (d) above, the heterocyclic ring is preferably 2-thiazole, 2-thiazoline, 2-oxazole, 2-oxazoline, 2-imidazole, 2-imidazoline, and 2-oxadiazole.

Further aspects of the invention include compounds of the formula

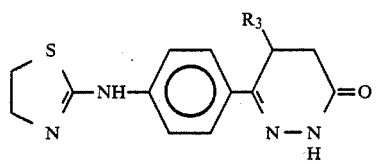

wherein $R_3$ is hydrogen or lower alkyl; compounds of the formula

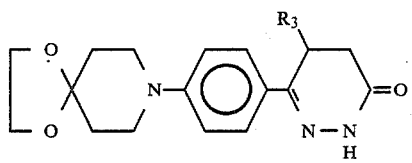

wherein $R_3$ is hydrogen or lower alkyl; compounds of the formula

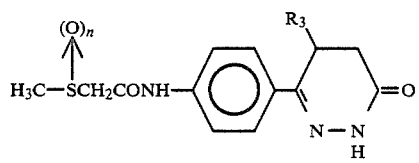

wherein $R_3$ is hydrogen or lower alkyl, and n is zero to two and the pharmaceutically acceptable salts thereof.

Particular aspects of the invention are the following compounds:
4,5-dihydro-6-[4-(4,5,6,7-tetrahydro-1H-benzimidazol-1-yl)-phenyl]-3(2H)-pyridazinone;
4,5-dihydro-6-[3-(1H-imidazol-1-yl)phenyl]-3(2H)-pyridazinone;
4,5-dihydro-6-(4-(1H-1,2,4-triazol-1-yl)phenyl]-3(2H)-pyridazinone;
4,5-dihydro-6-[4-(1H-benzimidazol-1-yl)phenyl]-3(2H)-pyridazinone;
4,5-dihydro-6-[4-(4-hydroxymethyl-1H-imidazol-1yl)-phenyl]-3(2H)-pyridazinone;
4,5-dihydro-6-[4-(2-methylthio-1H-imidazol-1-yl)phenyl]-3-(2H)-pyridazinone;
4,5-dihydro-6[4-(2-methylsulfinyl-1H-imidazol-1-yl)phenyl]-3(2H)-pyridazinone;
4,5-dihydro-6-[4-(2-methylsulfonyl-1H-imidazol-1-yl)phenyl]-3(2H)-pyridazinone;
6-[4-(4,5,6,7-tetrahydro-1H-benzimidazol-1-yl)phenyl]-3(2H)-pyridazinone;
6-[3-(1H-imidazol-1-yl)phenyl]-3(2H)-pyridazinone;
6-[4-(1H-1,2,4-triazol-1-yl)phenyl]-3(2H)-pyridazinone;
6-[4-(4-hydroxymethyl-1H-imidazol-1-yl)phenyl]-3(2H)-pyridazinone;
6-[4-(2-methylthio-1H-imidazol-1-yl)phenyl]-3(2H)-pyridazinone;
6-[4-[(4,5-dihydro-2-thiazolyl)amino]phenyl]-4,5-dihydro-3(2H)-pyridazinone;
4-amino-6-[4-(1H-imidazol-1-yl)-phenyl]-3(2H)-pyridazinone;
4,5-dihydro-6-[4-[1,4-dioxa-8-azaspiro[4,5]dec-8-yl]-phenyl]-3(2H)-pyridazinone;
2,3-dihydro-6-[4-(1H-imidazol-1-yl)phenyl]-3-oxo-4-pyridazine carbonitrile;
6-[4-(2-methylsulfinyl-1H-imidazol-1-yl)phenyl]-3(2H)-pyridazinone;
6-[4-(2-methylsulfonyl-1H-imidazol-1-yl)phenyl]-3(2H)-pyridazinone, and
6-[4-(1H-benzimidazol-1-yl)phenyl]-3(2H)-pyridazinone.

The present invention further relates to the method for increasing cardiac contractility in a patient requiring such treatment which comprises administering orally or parenterally in a solid or liquid dosage form to such patient an effective amount of a compound of the formula I, wherein ==== represents a double or single bond between two carbon atoms; Q is oxygen or sulfur; $R_2$ is hydrogen or lower alkyl; $R_3$ is hydrogen, lower alkyl, or when ==== represents a single bond, $R_3$ is di-lower alkyl, $R_4$ is hydrogen, lower alkyl or when ==== represents a double bond, $R_4$ is hydrogen, lower alkyl, amino, cyano, $CONR_aR_b$, hydroxy, $CH_2OH$, or

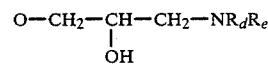

where $R_a$ and $R_b$ are independently H or lower alkyl, $R_c$ is lower alkyl or phenyl, and n is zero to two; or $R_3$ and $R_4$ taken together form a ring containing 1 to 4 carbon atoms; Y is H, halogen, lower alkyl, lower alkoxy, or a group such as $$O-CH_2-CH-CH_2-NR_dR_e$$
$$|$$
$$OH$$

where $R_d$ and $R_e$ are independently H, lower alkyl, $(CH_2)_nR_f$ where $R_f$ is a benzene ring optionally substituted by halogen, hydroxy, lower alkyl, lower alkoxy, and $CF_3$ and n is zero to three, and A is any of the groups from a–e and is attached to the 3- or 4-position of the phenyl ring:

a.

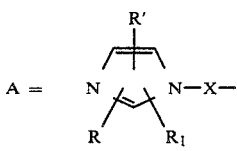

wherein $R_1$, $R'$, and $R$ are independently hydrogen or lower alkyl, $CH_2OH$, $SCH_3$, $SOCH_3$, $SO_2CH_3$, hydroxyalkyl, halogen, $(CH_2)_kNR''R'''$ wherein k is zero to two and $R''$ and $R'''$ are independently hydrogen or lower alkyl, wherein lower alkyl contains one to six carbon atoms; or when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkoxy, and (iii) pyridine ring; X is a bond, $(CH_2)_n$ or $O(CH_2)_{n+1}$ wherein n is one to four;

b.

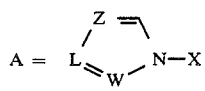

wherein
(i) $L=W=Z=CH$
(ii) $W=Z=N$ and $L=CH$ or
(iii) $L=Z=N$ and $W=CH$ and X is the same as defined in 1a.

c.

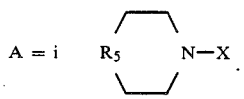

where $R_5$ is O, S, $NR_6$ wherein $R_6$ is hydrogen, lower alkyl, $COR_7$ where $R_7$ is a benzene ring optionally substituted by halogen, lower alkyl, hydroxy, lower alkoxy, and $CF_3$ or $(CH_2)_nR_7$ when n is zero to four and $R_7$ is the same as defined above, or (ii)

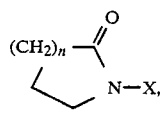

wherein n is one to three, or (iii)

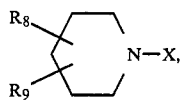

wherein $R_8$ and $R_9$ are independently hydrogen, lower alkyl, aryl, hydroxy, lower alkoxy, $NHR_{17}$ where $R_{17}$ is hydrogen, lower alkyl or lower alkanoyl, $CO_2R_{18}$ where $R_{18}$ is hydrogen or lower alkyl, $OCOBR_{10}$ where $R_{10}$ is lower alkyl, or phenyl, or phenyl substituted by halo, lower alkyl, lower alkoxy, or trifluoromethyl, and B is a direct bond or NH; or taken together are carbonyl or ethylenedioxy and the pharmaceutically acceptable salts thereof; in all instances, X is the same as defined in 1a;

d.

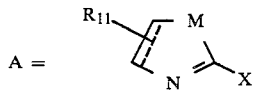

wherein ----- represents a double or single bond between two carbon atoms; $R_{11}$ is hydrogen or lower alkyl; M is NH, O, or S, and X is either a

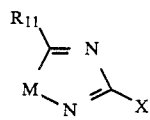

direct bond or NH or where X, M, and $R_{11}$ are the same as defined above, or e. $NHPR_{12}R_{13}$ wherein P is a bond or carbonyl; $R_{12}$ is lower alkyl, straight or branched; $R_{13}$ is $NR_{14}R_{15}$ wherein $R_{14}$ and $R_{15}$ are individually hydrogen, lower alkyl, straight or branched or taken together to form a 5-, 6-, or 7-membered ring or a group as defined in 1a–c; or $S(O)_nR_{16}$ where n is zero to two and $R_{16}$ is lower alkyl, straight or branched, phenyl and the pharmaceutically acceptable salts thereof.

Another aspect of the present invention relates to a cardiotonic composition for increasing cardiac contractility, said composition comprising an effective amount of a compound of formula I and a pharmaceutically acceptable carrier.

The process for producing pyridazinones of the formula I where $R_4$ is limited to hydrogen or lower alkyl, comprises reacting suitably substituted γ-oxobenzenbutanoic acids with suitably substituted hydrazines to give 4,5-dihydro-6-(substituted)phenyl-3(2H)-pyridazinones which can be dehydrogenated to the desired product by known dehydrogenation procedures such as bromination-dehydrobromination; by noble metal catalyzed dehydrogenation such as palladium-catalyzed dehydrogenation, or by oxidation-reduction procedures using $MnO_2$ or m-nitrobenzenesulphonic acid as the reagent according to the standard literature procedure set forth by W. V. Curran and A. Ross, *J. Med. Chem.*, 17, 273 (1974).

The compounds of formula (I) where A, Y, and $R_3$ have been defined above and $R_4$ is other than hydrogen or lower alkyl, are prepared by reacting suitably substituted $R_3$-oxobenzenebutanoic acids with benzylhydrazine to form compounds of the formula

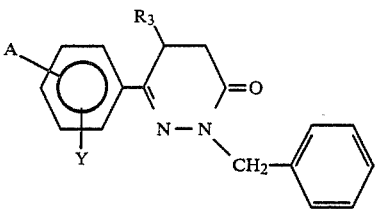

which is treated with phosphorus pentachloride and phosphorus oxychloride at elevated temperatures to afford compounds of the formula

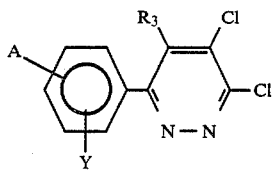

which on acid hydrolysis form compounds of the formula

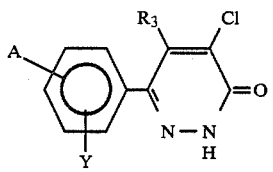

where the chlorine atom is displaced with cyano or $SR_c$ by treating the above compound with potassium cyanide or $R_cSH$. The cyano compounds may be converted to other $R_4$ groups by conventional methods known in the art.

Compounds of the formula I where A and Y have been defined above; $R_3$ is hydrogen and $R_4$ is other than hydrogen or lower alkyl may also be prepared by reacting a compound of the formula

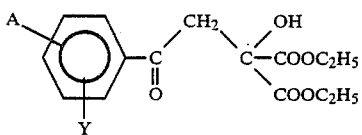

with hydrazine monohydrate at the boiling point of the solvent, which, for example, may be an alcohol such as methanol, to form the compound of the formula

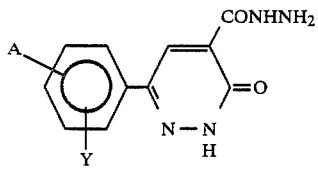

The resulting hydrazide may be converted by known methods to the group defined above for $R_4$.

Compounds of the formula I may also be prepared by converting known pyridazinone starting materials such as 6-(4-aminophenyl)-4,5-dihydro-3-(2H)-pyridazinone and/or (1,6-dihydro-6-oxo-3-pyridazinyl)-benzonitrile, described in German Patent Publication DT No. 2,150,685, to the desired compounds where A is defined above.

The compounds of the formula I where Q is sulfur may be conveniently prepared from the corresponding compounds of the formula I where Q is oxygen by treatment with phosphorus pentasulfide.

The compounds of formula (I) are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate, and the like respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The term "lower" in reference to alkyl and alkoxy means a straight or branched hydrocarbon chain of one to six carbon atoms such as, for example, methyl, ethyl, propyl, isopropyl, and the like. The term "halogen" includes fluorine, chlorine, bromine, and iodine but preferably is fluorine or chlorine.

The following Examples will further illustrate the invention without, however, limiting thereto.

EXAMPLE 1

Methyl 4-(1H-imidazol-1-yl)-β-oxobenzenepropanoate

A solution of 4-(1H-imidazol-1-yl)acetophenone (24.2 g, 0.13 mol) in tetrahydrofuran (250 ml) is added to a suspension of 50% NaH (6.7 g) in tetrahydrofuran (70 ml) with stirring. The solution is stirred at room temperature for one hour. Dimethylcarbonate (30 ml) is added followed by refluxing the mixture overnight. The solid is filtered off, the residue is treated wth water, and neutralized with acetic acid. The product is filtered and crystallized from methanol-ether to yield 15.0 g of the product methyl 4-(1H-imidazol-1-yl)-β-oxobenzenepropanoate.

EXAMPLE 2

4-(1H-Imidazol-1-yl-γ-oxobenzenebutanoic acid

A solution of methyl 4-(1H-imidazol-1-yl)-β-oxo-benzenepropanoate (6.1 g, 0.025 mol) in tetrahydrofuran (65 ml) is added slowly to a stirred suspension of 50% NaH (1.2 g, 0.025 mol) in tetrahydrofuran (20 ml) and the solution is stirred for one additional hour. Ethyl bromoacetate (4.5 g) is added followed by refluxing the mixture for seven to eight hours. The tetrahydrofuran is removed, the residue is treated with water, and the organic material is extracted with ether. The residue obtained after removal of the ether is hydrolysed by heating with 6N HCl for eight hours. The crude acid is finally crystallized from dimethylformamide to yield 3.3 g of the product 4-(1-imidazol-1-yl)-γ-oxobenzenebutanoic acid.

EXAMPLE 3

4,5-Dihydro-6-[4-(1H-imidazol-1-yl)phenyl]-3(2H)-pyridazinone (3a)

A solution of 4.5 g of 4-(1H-imidazol-1-yl)-γ-oxobenzenebutanoic acid in ethanol (60 ml) is heated under reflux with 85% hydrazine hydrate (2.5 ml) for 17 hours. The alcohol is evaporated off, the residue is treated with water and filtered. The crude product is finally crystallized from ethanol to yield 3.5 g of the product 4,5-dihydro-6-[4-(1H-imidazol-1yl)phenyl]-3(2H)-pyridazinone: mp 206°–207° C. (dec.)

Anal. Calcd for $C_{13}H_{12}N_4O$: C, 65.00; H, 5.00; N, 23.33. Found: C, 65.06, H, 5.35; N, 23.39.

Similarly, the reaction of 4-(2-methyl-1H-imidazol-1yl)-γ-oxobenzenebutanoic acid with hydrazine hydrate according to the procedure of this Example gives 4,5-dihydro-6-[4-(2-methyl-1H-imidazol-1-yl)phenyl]-3(2H)-pyridazinone (3b).

Similarly the reaction of 4-(2-phenyl-1H-imidazol-1-yl)-γ-oxobenzenebutanoic acid with hydrazine hydrate according to the procedure of this Example gives 4,5-dihydro-6-[4-(2-phenyl-1H-imidazol-1yl)phenyl]-3(2H)-pyridazinone (3c).

Similarly, reaction of 4-(2-ethyl-4-methyl-1H-imidazol-1-yl)-γ-oxobenzenebutanoic acid with hydrazine hydrate according to the procedure of this Example gives 4,5-dihydro-6-[4-(2-ethyl-4-methyl-1H-imidazol-1-yl)phenyl]-3(2H)-pyridazinone (3d).

Using the procedure of this Example, reaction of 4-(1H-imidazol-1-yl)-γ-oxobenzenebutanoic acid with methyl hydrazine and 2-hydroxethyl hydrazine gives 4,5-dihydro-6-[4-(1H-imidazol-1-yl)phenyl]-2-methyl-3-(2H)-pyridazinone (3e) and 4,5-dihydro-2(2-hydroxyethyl)-6-[4-(1H-imidazol-1-yl)phenyl]-3(2H)-pyridazinone (3f) respectively.

Similarly, the reaction of 4-(4-hydroxymethyl-1H-imidazol-1-yl)-γ-oxobenzenebutanoic acid with hydrazine hydrate according to the procedure of this Example gives 4,5-dihydro-6-[4-(4-hydroxymethyl-1H-imidazol-1-yl)phenyl]-3(2H)-pyridazinone (3g), mp 213.5°–215° C.

Similarly, the reaction of 4-(4,5-diethyl-1H-imidazol-1-yl)-γ-oxobenzenebutanoic acid with hydrazine hydrate according to the procedure of this Example gives 4,5-dihydro-6-[4-(4,5-diethyl-1H-imidazol-1-yl)phenyl]-3(2H)-pyridazinone (3h).

Similarly, the reaction of 4-(1H-benzimidazol-1-yl)-γ-oxobenzenebutanoic acid with hydrazine hydrate according to the procedure of this Example gives 4,5-dihydro-6-[4-(1H-benzimidazol-1-yl)phenyl]-3(2H)-pyridazinone (3i), mp 262°–264° C.

4,5-Dihydro-6-[4-(1H-imidazol-1-yl)phenyl]-5-methyl-3(2H)-pyridazinone (3j)

A suspension of KCN (6.6 g in 8 ml of water) is added slowly to a stirred solution of a mixture of 4-(1H-imidazol-1-yl)benzaldehyde (17.2 g), p-toluenesulfonic acid (19 g) and morpholine (11.4 g) in dioxane (100 ml). The mixture is refluxed for three hours, concentrated to half its volume and poured into saturated $K_2CO_3$ solution. The oil is extracted with $CH_2Cl_2$, the $CH_2Cl_2$ extract is washed with water, dried, and evaporated to yield an oil which is filtered through silica gel. The oil is finally crystallized from ether.

To a stirred solution of the above [4-(1H-imidazol-1-yl)phenyl]-4-morpholineacetonitrile in THF (120 ml) is added 30 drops of 30% KOH in methanol followed by a slow addition of crotononitrile (4.2 g) over a period of 15 minutes and the resulting reaction mixture is stirred at room temperature for 90 minutes. The reaction mixture is concentrated in vacuo, the residue is treated with water and the oil is extracted with $CH_2Cl_2$. The methylene chloride extract is washed with water, dried, and concentrated to yield a highly viscous gum.

This is dissolved in 30 ml of 6N HCl and heated on a steam bath for six hours. The reddish solution is evaporated to dryness in vacuo, the residue is taken up on 150 ml of absolute ethanol, heated on a steam bath for 15 minutes and cooled. The inorganic salts are filtered off and the filtrate is directly used in the next step. The filtrate is heated to reflux with 85% hydrazine hydrate (4 ml) for four hours. The solution is cooled, diluted with water, and filtered. The solid is crystallized from ethanol tetrahydrofuran to yield 2.8 g of the product 4,5-dihydro-6-[4-(1H-imidazol-1-yl)phenyl]-5-methyl-3(2H)-pyridazinone: (3j), mp 197°–198° C.

Anal. Calcd for $C_{14}H_{14}N_4O$: C, 66.12; H, 5.55; N, 22.04. Found: C, 66.12; H, 5.54; N, 21.05.

4,5-Dihydro-6-[4-(2-methylthio-1H-imidazol-1-yl)phenyl]-3(2H)-pyridazinone (3k)

A solution of 6-(4-aminophenyl)-4,5-dihydro-3-(2H)-pyridazinone (10 g, 0.053 mol) in N,N-dimethylformamide (200 ml) is added to an ice-cold solution of 1,1'-thiocarbonyldiimidazole (10 g, 0.056 mol) in N,N-dimethylformamide (50 ml) over a three hour period. The reaction mixture is slowly warmed up to room temperature and stirred for an additional half hour. The solution is diluted with 800 ml of water, cooled, filtered, and air-dried to give 10.8 g of the pure isothiocyanate, mp 111°–182.5° C.

A solution of 10 g of the above isothiocyanate in N,N-dimethylformamide (60 ml) is added dropwise to a solution of aminoacetaldehyde diethyl acetal (7.17 g) in N,N-dimethylformamide (20 ml) followed by heating for two hours at 80° C. The DMF is removed by distillation under reduced pressure and the residue is heated to reflux with 100 ml of 10% HCl for one half hour. Upon cooling, the solid is collected by filtration, washed with water, and finally crystallized to give 7 g of 4,5-dihydro-6-[4-(2-mercapto-1H-imidazol-1-yl)phenyl]-3(2H)-pyridazinone, mp 310°–312.5° (dec).

A solution of the above compound (2.97 g) in N,N-dimethylformamide (50 ml) is treated with CH₃I (4.6 g). The DMF is removed by distillation, and the residue is treated with water. The solution is then made basic and the crystalline material is collected by filtration to yield 1.75 g of the product 4,5-dihydro-6-[4-(2-methylthio-1H-imidazol-1-yl)phenyl]-3(2H)-pyridazinone, (3k), mp 155°–156° C.

A solution of 4,5-dihydro-6-[4-(2-methylthio-1H-imidazol-1-yl)phenyl]-3(2H)-pyridazinone (2.08 g) in chloroform (30 ml) is oxidized with m-chloroperbenzoic acid (1.56 g) at 0° C. to yield 1.45 g of the product 4,5-dihydro-6-[4-(2-methylsulfinyl-1H-imidazol-1-yl)phenyl]-3(2H)-pyridazinone (3l), mp 187°–188° C.

Similarly a solution of 4,5-dihydro-6-[4-(2-methylthio-1H-imidazol-1-yl)phenyl]-3(2H)-pyridazinone (1.68 g) in chloroform (15 ml) is oxidized with m-chloroperbenzoic acid (2.55 g) at ambient temperature to yield 1.54 g of the product 4,5-dihydro-6-[4-(2-methylsulfonyl-1H-imidazol-1-yl)phenyl-3(2H)-pyridazinone, (3m), mp 200°–201° C.

EXAMPLE 4

Methyl 3-(1H-imidazol-1-yl-β-oxobenzenepropanoate

A solution of 3-(1H-imidazol-1-yl)acetophenone (53.4 g, 0.28 mol) in tetrahydrofuran (300 ml) is added to a suspension of 60% NaH (11.6 g) in tetrahydrofuran (90 ml) with stirring. The solution is stirred at room temperature for one hour. Dimethylcarbonate (70 ml) is added followed by refluxing the mixture overnight. The solid is filtered off, the residue is treated with water, neutralized with acetic acid and the oil is extracted with ethyl acetate. The ethyl acetate extract is filtered through silica gel and evaporated to yield 29.8 g of the product methyl 3-(1H-imidazol-yl)-β-oxobenzenepropanoate.

EXAMPLE 5

3-(1H-Imidazol-1-y-)-γ-oxobenzenebutanoic acid

A solution of methyl 3-(1H-imidazol-1-yl)-β-oxobenzenepropanoate (29.1 g, 0.12 mol) in tetrahydrofuran (200 ml) is added slowly to a stirred suspension of 60% NaH (5.1 g, 0.12 mol) in tetrahydrofuran (75 ml) and the solution is stirred for one additional hour. Ethyl bromoacetate (21.1 g) is added following by refluxing the mixture for seven to eight hours. The tetrahydrofuran is removed, the residue is treated with water, and the organic material is extracted with ether. The residue obtained after removal of ether is hydrolysed by heating with 6N HCl for eight hours. The crude acid is crystallized from water to yield 12.3 g of the product 3-(1H-imidazol-1-yl)-γ-oxobenzenebutanoic acid, mp 140.5°–142° C.

EXAMPLE 6

4,5-Dihydro-6-[3-(1H-imidazol-1-yl)phenyl-3(2H)-pyridazinone

A solution of 5.2 g of 3-(1H-imidazol-1-yl)-γ-oxobenzenebutanoic acid in ethanol (60 ml) is heated under reflux with 85% hydrazine hydrate (1.8 g) for four hours. The alcohol is evaporated off, the residue is treated with water and filtered. The crude product is finally crystallized from ethanol to yield 2.9 g of the product 4,5-dihydro-6-[3-(1H-imidazol-1-yl)phenyl]-3(2H)-pyridazinone, mp 190°–190.5° C.

Anal. Calcd for $C_{13}H_{12}N_4O$: C, 64.98; H, 5.03; N, 23.39. Found: C, 65.02; H, 5.08; N, 23.33.

EXAMPLE 7

4-(4,5,6,7-Tetrahydro-1H-benzimidazol-1-yl)-γ-oxobenzenebutanoic acid

A solution of 4-fluoro-γ-oxobenzenebutanoic acid (20 g, 0.1 mol) and 5,6,7,8-tetrahydrobenzimidazole (12.2 g, 0.1 mol) in DMSO (50 ml) is added dropwise to a suspension of 50% NaH (9.6 g, 0.2 mol) in toluene (20 ml) with stirring keeping the temperature around 30° C. At this point, additional DMSO (50 ml) is added and the mixture is stirred at room temperature overnight followed by heating at 100°–110° C. for 18 hours. The solution is cooled, extracted with ether and the aqueous solution is adjusted to pH ~5. The solid thus obtained is filtered, washed with water and crystallized from DMF to give 10 g of the product 4-(4,5,6,7-tetrahydro-1H-benzimidazol-1-yl)-γ-oxobenzenebutanoic acid, mp 234°–235° C.

EXAMPLE 8

4,5-Dihydro-6-[4-(4,5,6,7-tetrahydro-1H-benzimidazol-1-yl)phenyl]-3(2H)-pyridazinone A mixture of 9 g of 4-(4,5,6,7-tetrahydro-1H-benzimidazol-1-yl)-γ-oxobenzenebutanoic acid and 3.5 g of hydrazine hydrate in 80 ml of ethanol is heated under reflux for six hours. The reaction mixture is allowed to cool and filtered. The crude product is finally crystallized from 2-methoxyethanol to yield 4.5 g of the product 4,5-dihydro-6-[4-(4,5,6,7-tetrahydro-1H-benzimidazol-1-yl)phenyl]-3(2H)-pyridazinone, mp 296°–297° C.

Anal. Calcd for $C_{17}H_{18}N_4O$, $0.1H_2O$: C, 68.88; H, 6.14; N, 18.90. Found: C, 68.84; H, 6.40; N, 18.50.

EXAMPLE 9

4,5-Dihydro-6-[4-(1H-1,2,4-triazol-1-yl)phenyl]-3(2H)-pyridazinone

A solution of 15 g of 4-(1H-1,2,4-triazol-1-yl)-γ-oxobenzenebutanoic acid [mp 234°–235° C., obtained from 4-(1H-1,2,4-triazol-1-yl)acetophenone according to the procedure of Examples 1 and 2] in ethanol (100 ml) is heated under reflux with 85% hydrazine hydrate (5.4 g) for six hours. The reaction mixture is allowed to cool and the solid is filtered, washed successively with dilute NaHCO₃ solution, water, and finally crystallized from DMF to give 8.3 g of the product 4,5-dihydro-6-[4-(1H-1,2,4-triazol-1-yl)phenyl]-3(2H)-pyridazinone, mp 311°–312° C. (dec).

Anal. Calcd for $C_{12}H_{11}N_5O$, 0.1 DMF: C, 59.43; H, 4.74; N, 28.74. Found: C, 59.30; H, 4.59; N, 28.85.

EXAMPLE 10

4,5-Dihydro-6-[4-(4H-1,2,4-triazol-4-yl)phenyl]-3(2H)-pyridazinone

A mixture of 6-(4-aminophenyl)-3(2H)-pyridazinone (3.78 g, 0.02 mol) and diformylhydrazine (1.76, 0.02 mol) are heated together at 220° C. for six hours. The solid mass is chromatographed and finally crystallized from acetonitrile/methanol to yield the product 4,5-dihydro-6-[4-(4H-1,2,4-triazol-4-yl)phenyl]-3(2H)-pyridazinone, mp 292.5°–293° C. (dec).

Anal. Calcd for $C_{12}H_{11}N_5O$: C, 59.75; H, 4.60; N, 29.03. Found: C, 59.66; H, 4.61; N, 29.27.

EXAMPLE 11

4,5-Dihydro-6-[4-(1H-pyrrol-1-yl)phenyl]-3(2H)-pyridazinone

A mixture of 6-(4-aminophenyl)-3(2H)-pyridazinone (3.7 g) and 2,5-dimethoxytetrahydrofuran (2.6 g) in glacial acetic acid (37 ml) is heated under reflux for four hours. The reaction mixture is cooled, filtered and the solid is washed with ethanol, and finally crystallized from methanol to give 1.2 g of the product, 4,5-dihydro-6-[4-(1H)-pyrrol-1-yl)phenyl]-3(2H)-pyridazinone, mp 222°–223° C.

Anal. Calcd for $C_{14}H_{13}N_3O$: C, 70.27; H, 5.48; N, 17.56. Found: C, 70.50; H, 5.40; N, 17.60.

EXAMPLE 12

4,5-Dihydro-6-[4-[2-(1H-imidazol-1-yl)ethoxy]phenyl]-3(2H)-pyridazinone

Potassium-t-butoxide (0.56 g, 0.5 mmol) is added to a solution of imidazole (0.34 g, 0.5 mmol) in dry DMF (10 ml) under $N_2$. The resulting mixture is stirred until homogeneous and then five minutes longer. A solution of 4,5-dihydro-6-(2-chloroethoxyphenyl)-3(2H)-pyridazinone (1.27 g, 0.5 mmol) in dry DMF (20 ml) is added in one portion and the resultant mixture is heated and stirred at 60° for 12 hours. The DMF is then distilled off and the residue taken up in chloroform. The chloroform solution is extracted with 5% aqueous HCl. The aqueous extract is made basic with 10% aqueous sodium carbonate and extracted several times with methylene chloride. The methylene chloride is evaporated, leaving behind 0.45 g of the product 4,5-dihydro-6-[4-(2-(1H-imidazol-1-yl)ethoxyphenyl]-3(2H)-pyridazinone as an amorphous solid.

EXAMPLE 13

6-[4-(1H-Imidazol-1-yl)phenyl]-3(2H)-pridazinone (13a)

Bromine (1.6 ml) is added dropwise to a solution of 4,5-dihydro-6-[4-(1H-imidazol-1-yl)phenyl]-3(2H)-pyridazinone (3.5 g) in acetic acid (25 ml) at 80° C. The mixture is heated for six hours to complete the reaction. The solid is filtered, washed with ether, and converted to the free base which is crystallized from ethanol to yield 1.1 g of the product 6-[4-(1H-imidazol-1-yl)phenyl]-3(2H)-pyridazinone, mp 244°–245° C.

Anal. Calcd for $C_{13}H_{10}N_4O$, $1/5H_2O$: C, 64.56; H, 4.30; N, 23.27; $H_2O$, 1.49. Found: C, 64.30; H, 4.36; N, 23.04; $H_2O$, 1.11.

Similarly, reaction of 4,5-dihydro-6-[4-(2-methyl-1H-imidazol-1-yl)phenyl]-3(2H)-pyridazinone with bromine in acetic acid as described in this Example gives 6-[4-(2-methyl-1H-imidazol-1-yl)phenyl)-3(2H)-pyridazinone (13b).

Similarly, reaction of 4,5-dihydro-6-[4-(2-phenyl-1H-imidazol-1-yl)phenyl-3(2H)-pyridazinone with bromine in acetic acid as described in this Example gives 6-[4-(2-phenyl-1H-imidazol-1H-imidazol-1-yl)phenyl]-3(2H)-pyridazinone (13c).

Similarly, reaction of 4,5-dihydro-6-[4-(2-ethyl-4-methyl-1H-imidazol-1-yl)phenyl]-3(2H)-pyridazinone with bromine in acetic acid as described in this Example gives 6-[4-(2-ethyl-4-methyl-1H-imidazol-1-yl)phenyl-3(2H)-pyridazinone (13d).

Using the procedure of this Example, reaction of 4,5-dihydro-2-methyl-6-[4-(1H-imidazol-1-yl)phenyl]-3(2H)-pyridazinone and 4,5-dihydro-2-(2-hydroxyethyl)-6-[4-(1H-imidazol-1-yl)phenyl]-3(2H)-pyridazinone with bromine in acetic acid gives 6-[4-1H-imidazol-1-yl)phenyl]-2-methyl-3(2H)-pyridazinone (13e) and 2-(2-hydroxyethyl)-6-[4-1H-imidazol-1-yl)phenyl]-3(2H)-pyridazinone respectively (13f).

Similarly, reaction of 4,5-dihydro-6-[4-(4,5-diethyl-1H-imidazol-1-yl)phenyl]-3(2H)-pyridazinone with bromine in acetic acid as described in this Example gives 6-[4-(4,5-diethyl-1H-imidazol-1-yl)phenyl)-3(2H)-pyridazinone (13g).

Similarly, reaction of 4,5-dihydro-6-[4-1H-benzimidazol-1-yl)phenyl]-3(2H)-pyridazinone with bromine in acetic acid as described in this Example gives 6-[4-1H-benzimidazol-1-yl)phenyl]-3(2H-pyridazione (13h).

6-[4-(1H-Imidazol-1-yl)phenyl]-5-methyl-3(2H)-pyridazinone (13i)

A solution of 3.6 g of 4,5-dihydro-6-[4-(1H-imidazol-1-yl)phenyl]-5-methyl-3(2H)-pyridazinone in a mixture of dioxane (100 ml) and N,N-dimethylformamide (25 ml) is heated with 12 g of $MnO_2$ at 90° C. overnight. The temperature is raised to 105° C. and maintained there for four hours. The inorganic solid is filtered off and washed thoroughly with hot dioxane. The filtrate and the washings are combined, evaporated in vacuo, and the residue is crystallized from methanol and tetrahydrofuran to yield 2.1 g of the product, 6-[4-(1H-imidazol-1-yl)phenyl]-5-methyl-3-(2H)pyridazinone, mp 284°–286° C.

Anal. Calcd for $C_{14}H_{12}N_4O$: C, 66.65; H, 4.79; N, 22.21. Found: C, 66.22, H, 4.59; N, 22.06.

EXAMPLE 14

6-[3-(1H-Imidazol-1-yl)phenyl]-3(2H)-pyridazinone

A solution of bromine (0.7 ml) in acetic acid (20 ml) is added dropwise to a solution of 2.6 g of 4,5-dihydro-6-[3-(1H-imidazol-1-yl)phenyl-3(2H)-pyridazinone in acetic acid (85 ml) at 90°–95°. The reaction mixture is heated to reflux for 3.5 hours. Upon cooling, the solid is filtered, washed with ether, and converted to the free base which is crystallized from ethanol to yield 1.3 g of the product 6-[3-(1H-imidazol-1-yl)phenyl]-3-(2H)-pyridazinone, mp 234.5°–235.5° C.

Anal. Calcd for $C_{13}H_{10}N_4O$: C, 65.53; H, 4.23; N, 23.52. Found: C, 65.44, H, 4.66; N, 23.73.

EXAMPLE 15

6-[4-(4,5,6,7-Tetrahydro-1H-benzimidazol-1-yl)phenyl]-3(2H)-pyridazinone

A solution of bromine (1 g) in 10 ml of acetic acid is added dropwise to a solution of 1.6 g of 4,5-dihydro-6-

[4-(4,5,6,7-tetrahydro-1H-benzimidazol-1-yl)phenyl]-3(2H)-pyridazinone in 40 ml of acetic acid at 86°–88° C. The mixture is subsequently heated at 100° C. for four to five hours. The reaction mixture is cooled, the solid is filtered off, washed with ether, and air dried. The hydrobromide salt thus obtained is converted to the free base which is crystallized from ethanol to give 0.6 g of the product 6-[4-(4,5,6,7-tetrahydro-1H-benzimidazol-1-yl)phenyl]-3(2H)-pyridazinone, mp 266°–267° C.

Anal. Calcd for $C_{17}H_{16}N_4O$, $0.1H_2O$: C, 69.35; H, 5.50; N, 19.03. Found: C, 69.25; H, 5.36; N, 19.03.

EXAMPLE 16

6-[4-[2-(1H-Imidazol-1-yl)ethoxy]phenyl]-3(2H)-pyridazinone

A solution of bromine (0.6 g) in acetic acid (6 ml) is added dropwise to a solution of 4,5-dihydro-6-[4-[2-(1H-imidazol-1-yl)ethoxy]phenyl]-3(2H)-pyridazinone (2.84, 0.01 mol) in acetic acid (56 ml) at 90° C. The mixture is subsequently heated at 100° C. for four hours. The reaction mixture is cooled, the solid is filtered off, washed with ether, and air dried. The hydrobromide salt thus obtained is converted to the free base which is crystallized from ethanol to give 1.2 g of the product 6-[4-[2-(1H-imidazol-1-yl)ethoxy]phenyl]-3(2H)-pyridazinone.

EXAMPLE 17

N-[[[4-(1,4,5,6-Tetrahydro-6-oxo-3-pyridazinyl)phenyl]amino]thioxomethyl]benzamide To a solution of 0.8 g of ammonium thiocyanate in 5 ml of hot acetone is added dropwise 1.4 g of benzoyl chloride. After the initial reaction subsides the reaction mixture is heated to reflux for 15 minutes when the benzoylisothiocyanate crystallized. A solution of 1.89 g of 6-(4-amino)phenyl-3(2H)-pyridazinone in 20 ml of hot DMF is added to the above reaction mixture with stirring followed by heating at 100° C. for six hours. The reaction mixture is cooled, poured into water, and filtered to yield 2 g of N-[[[4-(1,4,5,6-tetrahydro-6-oxo-3-pyridazinyl)phenyl]amino]thioxomethyl]benzamide mp 232°–233° dec.

Anal. Calcd for $C_{18}H_{16}N_4O_2S$: C, 61.36; H, 4.54; N, 15.90; S, 9.09. Found: C, 61.19; H, 4.69; N, 16.01; S, 9.07.

EXAMPLE 18

N-[4-(1,4,5,6-Tetrahydro-6-oxo-3-pyridazinyl)phenyl]thiourea

To a suspension of 0.7 g of N-[[[4-(1,4,5,6-tetrahydro-6-oxo-3-pyridazinyl)phenyl]amino]thioxomethyl]benzamide in 7 ml of ethanol is added 1.6 ml of 10% ethanolic sodium hydroxide followed by heating for two hours. The reaction mixture is cooled, diluted with water, and filtered to give 0.4 g of the product, N-[4-(1,4,5,6-tetrahydro-6-oxo-3-pyridazinyl)phenyl]thiourea mp 234°–235° C.

Anal. Calcd for $C_{11}H_{12}N_4OS$: C, 53.22; H, 4.81; N, 22.58. Found: C, 53.32; H, 4.91; N, 22.32.

EXAMPLE 19

4,5-Dihydro-6-[4-(2-imidazolidinylideneamino)phenyl]-3(2H)-pyridazinone

A solution of 2.8 g of N-[4-(1,4,5,6-tetrahydro-6-oxo-3-pyridazinyl)phenyl]thiourea in 20 ml of DMF at 80° C. is treated with a solution of 3.0 g of methyl iodide in 10 ml of DMF and the reaction mixture is stirred for two hours. The DMF is distilled under reduced pressure and the residue is treated with ethanol and filtered to give 2.4 g of the isothiouronium salt as off-white solid which is used directly for cyclization.

A mixture of 2.3 g of the above isothiouronium salt and 1.0 g of ethylenediamine in 20 ml of EtOH is heated to reflux for two hours. The solution is concentrated to a small volume and the solid is filtered, washed with ethanol, and air-dried to yield 0.7 g of the product, 4,5-dihydro-6-[4-(2-imidazolidinylideneamino)phenyl]-3(2H)-pyridazinone, mp 235°–236° C.

Anal. Calcd for $C_{13}H_{15}N_5O$: C, 60.68; H, 5.88; N, 27.22. Found: C, 60.51; H, 5.94; N, 27.25

EXAMPLE 20

4,5-Dihydro-6-[4-(isothiocyano)phenyl]-3(2H)-pyridazinone

A solution of 10.0 g of 6-(4-aminophenyl)-4,5-dihydro-3(2H)-pyridazinone in 200 ml of DMF is added dropwise over a period of three hours to a stirred solution of 10.5 g of 1,1-thiocarbonyldiimidazole while cooling in an ice-water bath. After completion of the addition, stirring is continued for 30 minutes at icebath temperature followed by an additional 30 minutes at room temperature. The reaction mixture is filtered and the filtrate is diluted with 500 ml of water. The aqueous suspension is cooled in ice and the solid is filtered, washed with water, and dried to yield 10.8 g of the product, 4,5-dihydro-6-[4-(isothiocyano)phenyl]3(2H)-pyridazinone as off-white powder, mp 181.5°–183° C.

Anal. Calcd for $C_{11}H_9N_3OS$: C, 57.13; H, 3.92; N, 18.17; S, 13.86. Found: C, 57.36; H, 4.02; N, 18.47; S, 13.69.

EXAMPLE 21

6-[4-[(4,5-Dihydro-2-thiazolyl)amino]phenyl]-4,5-dihydro-3(2H)-pyridazinone

A mixture of 0.57 g of 4,5-dihydro-6-[4-(isothiocyano)phenyl]-3(2H)-pyridazinone, 0.51 g of 2-bromoethylamine hydrobromide and 0.34 g of anhydrous $K_2CO_3$ in 12 ml of DMF is heated at 80° C. for four hours. The reaction mixture is cooled, filtered, and the filtrate is concentrated under reduced pressure. The residue is treated with water, neutralized, and filtered to give 0.5 g of 6-[4-[(4,5-dihydro-2-thiazolyl)amino]phenyl]-4,5-dihydro-3(2H)-pyridazinone, mp 217°–218° C.

Anal. Calcd for $C_{13}H_{14}N_4OS$: C, 56.93; H, 5.10; N, 20.43; S, 11.67. Found: C, 56.60; H, 5.13; N, 20.13; S, 11.43.

EXAMPLE 22

N-(2-Chloroethyl)-N'-[4-(1,4,5,6-tetrahydro-6-oxo-3-pyridazinyl)phenyl]urea

A mixture of 1.89 g of 6-(4-amino)phenyl-3(2H)-pyridazinone, 1.1 g of 2-chloroethyl isocyanate in 20 ml of DMF is heated at 80° C. for four hours. The DMF is distilled under reduced pressure and the residue is treated with water. The solid is filtered, washed with water and air-dried to give 2.5 g of N-(2-chloroethyl)-N'-[4-(1,4,5,6-tetrahydro-6-oxo-3-pyridazinyl)phenyl]urea, mp 212°–213° dec.

Anal. Calcd for $C_{13}H_{15}ClN_4O_2$: C, 52.97; H, 5.09; N, 19.01; Cl, 12.05. Found: C, 53.28; H, 5.14; N, 19.01; Cl, 11.75.

EXAMPLE 23

6-[4-[(4,5-Dihydro-2-oxazolyl)amino]phenyl]-4,5-dihydro-3(2H)-pyridazinone

A mixture of 1.8 g of N-(2-chloroethyl)-N'-[4-(1,4,5,6-tetrahydro-6-oxo-3-pyridazinyl)phenyl]-urea and 0.7 g of NaOMe in 20 ml of DMF is heated at 100° C. for five hours. The DMF is distilled under reduced pressure, the residue is treated with water, and the pH of the solution is adjusted to 6. The solid is filtered, washed with water, and crystallized from DMF to yield 1.2 g of the product, 6-[4-[(4,5-dihydro-2-oxazolyl)amino]phenyl]-4,5-dihydro-3(2H)-pyridazinone, mp 332°–333° C.

Anal. Calcd for $C_{13}H_{14}N_4O_2$: C, 60.45; H, 5.46; N, 21.70. Found: C, 60.30; H, 5.58; N, 21.81.

EXAMPLE 24

4,5-Dihydro-6-[4-[(4-methyl-2-thiazolyl)amino]phenyl]-3(2H)-pyridazinone

A mixture of 1.2 g of N-[4-(1,4,5,6-tetrahydro-6-oxo-3-pyridazinyl)phenyl]thiourea and 0.5 g of chloroacetone in 20 ml of DMF is heated on a steambath for four hours. The DMF is distilled under reduced pressure and the residue is treated with water. The pH of the solution is adjusted to 8 and the solution is filtered. The residue is crystallized from DMF to yield 0.8 g of the product, 4,5-dihydro-6-[4-[(4-methyl-2-thiazolyl)amino]phenyl]-3(2H)-pyridazinone, mp 306°–307° C.

Anal. Calcd for $C_{14}H_{14}N_4OS$: C, 58.74; H, 4.89; N, 19.58. Found: C, 58.51; H, 4.98; N, 19.68.

By substituting chloroacetaldehyde instead of chloroacetone in Example 24 one obtains 4,5-dihydro-6-[4-[(2-thiazolyl)amino]phenyl-3(2H)-pyridazinone.

EXAMPLE 24a 4,5-Dihydro-6-[4-(4-methyl-2-thiazolyl)phenyl]-3(2H)-pyridazinone mp 266°–267° C. is obtained by following the procedure described above in Example 24 using a molar equivalent quantity of 4-(1,6-dihydro-6-oxo-3-pyridazinyl)benzenecarbothioamide in place of N-[4-(1,4,5,6-tetrahydro-6-oxo-3-pyridazinyl)phenyl]-thiourea.

EXAMPLE 24b 4,5-Dihydro-6-[4-(2-thiazolyl)phenyl]-3(2H)-pyridazinone, mp 265°–266° C., is obtained by following the procedure described above in Example 24 using 2.3 g of 4-(1,6-dihydro-6-oxo-3-pyridazinyl)benzenecarbothioamide, 2.6 g of chloroacetaldehyde, 30 ml of DMF, and a heating period of two hours.

EXAMPLE 25

6-[4-(4,5-Dihydro-2-thiazolyl)phenyl]-4,5-dihydro-3(2H)-pyridazinone

A solution of 3.5 g of 4-(1,6-dihydro-6-oxo-3-pyridazinyl)benzenecarbothioamide, 3.1 g of 1,2-dibromoethane in 75 ml of DMF containing 4.2 g of $K_2CO_3$ is heated on a steambath for three hours. The inorganic salts are filtered and the filtrate is evaporated under reduced pressure. The residue is crystallized from ethanol/tetrahydrofuran to yield 1.2 g of the product, 6-[4-(4,5-dihydro-2-thiazolyl)phenyl]-4,5-dihydro3(2H)-pyridazinone mp 236°–238° C.

Anal. Calcd for $C_{13}H_{13}N_3OS$: C, 60.21; H, 5.04; N, 16.20. Found: C, 60.27; H, 5.27; N, 16.21.

EXAMPLE 26

6-[4-(4,5-Dihydro-1H-imidazol-2-yl)phenyl]-4,5-dihydro-3(2H)-pyridazinone

A slurry of 3 g of 4-(1,6-dihydro-6-oxo-3-pyridazinyl)benzenecarbothioamide in 5 ml of ethylenediamine is heated at 100° C. for 30 minutes when a clear solution is obtained. The solution is poured into 50 ml of ice-water and the solid is filtered, washed with a small volume of ice-water, and air-dried to give 2.5 g of the product, 6-[4-(4,5-dihydro-1H-imidazol-2-yl) phenyl]-4,5-dihydro-3(2H)-pyridazinone, mp 296°–297° dec.

Anal. Calcd for $C_{13}H_{14}N_2O$: C, 64.44; H, 5.82; N, 23.13. Found: C, 64.24; H, 5.84; N, 23.48.

EXAMPLE 27

4,5-Dihydro-6-[4-(5-methyl-1,2,4-oxadiazol-3-yl)phenyl]-3(2H)-pyridazinone

To a stirred preheated solution of 2.5 g of 4-(1,6-dihydro-6-oxo-3-pyridazinyl)benzonitrile [prepared by following the procedure described in William V. Curran and Adma Ross, *J. Med. Chem.*, 17, 273 (1974)]in 50 ml of ethanol is added a solution of 2.1 g of hydroxylamine hydrochloride and 2.8 g of $K_2CO_3$ in 25 ml of water and the solution is heated to reflux for 1.5 hours. The reaction mixture is cooled and the solid is filtered, washed with water, and airdried to yield 2.8 g of the amidoxime, mp 265°–265° C.

Anal. Calcd for $C_{11}H_{12}N_4O_2$: C, 56,89; H, 5.21; N, 24.13. Found: C, 56.96; H, 5.11; N, 24.20.

A solution of 2.8 g of the above amidoxime in 25 ml of pyridine containing 2 ml of acetic anhydride is heated at 80° C. for two hours. The pyridine is distilled under reduced pressure and the residue is triturated with acetonitrile. The solid thus obtained is filtered to give 1.8 g of the corresponding acetate, mp 168°–169° dec.

A solution of 1.7 of the above ester in 15 ml of pyridine and 15 ml of acetic anhydride is heated to reflux for two hours. The solution is evaporated under reduced pressure and the residue is crystallized from methanol to yield 0.7 g of the product, 4,5-dihydro-6-[4-(5-methyl-1,2,4-oxadiazol-3-yl)phenyl]-3(2H)-pyridazinone mp 209°–211° C.

Anal. Calcd for $C_{13}H_{12}N_4O_2$: C, 60.93; H, 4.98; N, 21.87. Found: C, 61.02; H, 4.86; N, 21.88.

EXAMPLE 28

4-(1,6-Dihydro)-6-oxo-3-pyridazinyl)benzenecarbothioamide

Hydrogen sulfide is bubbled slowly for eight minutes to a solution of 4-(1,6-dihydro-6-oxo-3-pyridazinyl)benzonitrile in 75 ml of DMF containing 1.8 g of ethylenediamine and the reaction mixture is allowed to stand for one hour at room temperature when a white precipitate begins to separate. The precipitate is filtered and the filtrate is poured into 300 ml of cold water. Filtration affords 3.8 g of a yellow crystalline product, 4-(1,6-dihydro)-6-oxo-3-pyridazinyl)benzthioamide, mp 255°–256° dec.

Anal. Calcd for $C_{11}H_{11}N_3OS$: C, 56.64; H, 4.74; N, 18.02. Found: C, 56.64; H, 4.56; N, 18.24.

EXAMPLE 29

Hydroxy[2-[4-(1H-imidazol-1-yl)-phenyl]-2-oxoethyl]-propanedioic acid diethyl ester A mixture of diethylketomalonate (87.08 g, 0.50 mole) and 4-(imidazol-1-yl)acetophenone (93.1 g, 0.50 mole) is warmed to 95°–100° C. with stirring for three hours. During this time, the original tan slurry is transformed into a black syrup. At the end of three hours, anhydrous ethanol (130 ml) is added with stirring, resulting in a black solution. This solution is cooled to room temperature, an aliquot is removed and scratched to induce crystallization, and the crystals thus obtained returned to the cool solution. Upon standing overnight at 8° C., the solution forms a solid mass, which is suspended in absolute ethanol (100 ml) and filtered to obtain a brownish solid, which is dried at 43° in a vacuum oven for four hours to yield 67 g hydroxy [2-[4-(1H-imidazol-1-yl)-phenyl]-2-oxoethyl]propanedioic acid diethyl ester. Material thus obtained is suitable for use without additional purification, however, it can be recrystallized from methanol to give pure product, mp 155°–156° C.

Anal. Calcd for $C_{18}H_{20}N_2O_6$: C, 60.00; H, 5.60; N, 7.77. Found: C, 60.03; H, 5.69; N, 7.80.

EXAMPLE 30

2,3-Dihydro-6-[4-(1H-imidazol-1-yl)-phenyl]-3-oxo-4-pyridazinecarboxylic acid hydrazide A solution of hydrazine monohydrate (79.1 g, 77 ml, 1.58 mole), hydroxy[2-[4-(1H-imidazol-1-yl)-phenyl]-2-oxoethyl]-1-propanedioic acid diethyl ester (113.7 g, 0.316 mole), in methanol (700 ml) is heated under reflux for 18 hours. At the end of this time, the reaction mixture is cooled in ice, the resulting crystalline yellow solid is filtered, washed with methanol (60 ml), and dried at 78° in a vacuum oven 18 hours to yield 80.2 g of of 2,3-dihydro 6-[4-(1H-imidazol-1-yl)-phenyl]-3-oxo-4-pyridazinecarboxylic acid hydrazide; mp 304°–305° C., dec.

Anal. Calcd for $C_{14}H_{12}N_6O_2$: C, 56.75; H, 4.08; N, 28.36. Found: C, 56.92; H, 4.46; N, 27.90.

EXAMPLE 31

4-amino-6-[4-(1H)-imidazol-1-yl)-phenyl]-3(2H)-pyridazinone

A slurry of 6-[4-(1H-imidazol-1-yl)-phenyl]-3(2H)-pyridazinone-4-carboxylic acid hydrazide (10.0 g, 0.034 mole), water (111 ml), and 12N hydrochloric acid (195 ml) is cooled to 5° C. with stirring, and treated with the dropwise addition of a solution of sodium nitrite (5.6 g, 0.08 mole) in water (20 ml). When the addition is complete, the reaction mixture is warmed to 20° C., transferred to a large beaker, and warmed on a steam bath. As it heats, the reaction mixture forms a solution, and a precipitate separates. The cooled reaction mixture is filtered and the filtrate made basic with the addition of concentrated ammonia (250 ml). The resulting suspension is filtered and the solid thus obtained is combined with the first crop and dried at 68° in a vacuum oven for 24 hours. The solid is a mixture of the desired amine and starting carboxylic acid. The amine is separated from the acid by silica gel filtration using chloroform:methanol: concentrated ammonium hydroxide 90:10:1 as the solvent. The elutate is concentrated to a small volume, and 1.12 g of 4-amino-6-[4-(1H)-imidazol-1-yl)-phenyl]-3(2H)-pyridazinone, mp 323°–325° C., dec., is isolated by filtration.

Anal. Calcd for $C_{13}H_{11}N_5O$: C, 61.65; H, 4.38; N, 27.65. Found: C, 61.31; H, 4.61; N, 27.43.

EXAMPLE 32

2,3-Dihydro-6-[4-(1H-imidazol-1-yl)-phenyl]-3-oxo-4-pyridazinecarboxamide

Procedure A

A suspension of 6-[4-(1H-imidazol-1-yl)-phenyl]-3(2H)-pyridazinone-4-carboxylic acid hydrazide (5.0 g, 0.017 mole) in water (37.5 ml) is treated with a solution of potassium ferricyanide (10.1 g, 0.03 mole) in concentrated ammonia (51 ml) added portionwise. When gas evolution ceases, the reaction mixture is treated with additional potassium ferricyanide (5.05 g, 0.0154 moles) in concentrated ammonia (22 ml) added in one portion. After ten minutes of stirring, the resulting suspension is filtered. The solid is air dried, recrystallized from ethanol, collected by filtration, and dried at 60° C. in a vacuum oven for 48 hours to yield 1.55 g of 2,3-dihydro-6-[4-(1H-imidazol-1-yl)-phenyl]-3-oxo-4-pyridazinecarboxamide, mp 332°–335° C., dec.

Anal. Calcd for $C_{14}H_{11}N_5O_2$: C, 59.78; H, 3.94, N, 24.90. Found: C, 59.51; H, 4.16; N, 24.59.

Procedure B

A slurry of triethylamine (50.8 g, 70 ml, 0.5 mole), thionyl chloride (39.4 g, 24 ml, 0.33 mole), 6-[4-(1H-imidazol-1-yl)-phenyl]-3(2H)-pyridazinone-4-carboxylic acid (26.3 g, 0.08 mole) and N,N-dimethylformamide (500 ml) is prepared with cooling, adding the triethylamine last with vigorous stirring. After one hour, the mixture is added with vigorous stirring to N,N-dimethylformamide (250 ml) through which a stream of gaseous ammonia is introduced through a coarse-frit sparge tube. When ammonia ceases to be absorbed, the reaction mixture is evaporated to dryness and filtered through a column (3×15 cm) of neutral alumina (activity I), eluted with 10% methanol in methylene chloride to yield a tan waxy solid. This solid is triturated with ethanol, filtered, and dried at 100° in a vacuum oven 60 hours to yield 11.6 g of 2,3-dihydro-6-[4-(1H-imidazol-1-yl)-phenyl]-3-oxo-4-pyridazinecarboxamide, mp 333°–334° C., dec.

EXAMPLE 33

2,3-Dihydro-6-[4-(1H-imidazol-1-yl)-phenyl]-3-oxo-4-pyridazinecarboxylic acid

A suspension of 6-[4-(1H-imidazol-1-yl)-phenyl-3(2H)-pyridazinone-4-carboxylic acid hydrazide (25.0 g, 0.08 mole) in 12N hydrochloric acid (2500 ml) is heated under reflux for 18 hours. The reaction mixture is cooled in ice, filtered, and the collected solid is washed with 6N hydrochloric acid (350 ml) followed by diethyl ether (2×25 ml). The solid is dried at 45° in a vacuum oven for 18 hours to yield 22.7 g of 2,3-dihydro-6-[4-(1H-imidazol-1-yl)-phenyl]-3-oxo-4-pyridazinecarboxylic acid as the hydrochloride salt, mp 290°–292° C., dec.

Anal. Calcd for $C_{14}H_{11}N_4O_3Cl$: C, 52.76; H, 3.48; N, 17.58; Cl, 11.12. Found: C, 52.63; H, 3.66; N, 17.68; Cl, 10.64.

EXAMPLE 34

2-(Methylthio)-N-[4-(1,2,5,6-tetrahydro-6-oxo-3-pyridazinyl)phenyl]acetamide

The pH of a solution of 1.17 g of methylthioacetic acid and 1.89 g of 6-(4-aminophenyl)-4,5-dihydro-3(2H)-pyridazinone in 750 ml of water is adjusted to 5 with 2N sodium hydroxide solution. After the addition of 1.55 g of 1-ethyl-3-(3-dimethylamino)propyl carbodiimide hydrochloride, the pH was maintained at 5 by the addition of 1N hydrochloric acid for 1.5 hours and stirring was continued for 70 hours. Filtration affords 2.1 g of a crystalline solid mp 190°–220°. Trituration with ethanol gives an analytical sample, mp 239°–240°.

Anal. Calcd for $C_{13}H_{15}N_3O_2S$: C, 56.31; H, 5.45; N, 15.16; S, 11.45. Found: C, 56.08; H, 5.25; N, 15.23; S, 11.69.

2-(Methylsulfinyl)-N-[4-(1,2,5,6-tetrahydro-6-oxo-3-pyridazinyl)phenyl]acetamide To a solution of 0.69 g of 2-(methylthio)-N-[4-(1,4,5,6-tetrahydro-6-oxo-3-pyridazinyl)phenyl]acetamide in 800 ml of water is added a solution of 0.50 g (85%) of m-chloroperbenzoic acid at 12°. After this addition is completed the temperature is held at 12° for one hour and then at 20°–25° for 20 hours. There is deposited 0.55 g of a crystalline compound, mp 239° dec. Recrystallization from methanol affords an analytical sample, mp 254° dec.

Anal. Calcd for $C_{13}H_{15}N_3O_3S$: C, 53.24; H, 5.16; N, 14.33; S, 10.91. Found: C, 53.31; H, 5.17; N, 14.41; S, 11.09.

EXAMPLE 35

N-[4-(1,4,5,6-Tetrahydro-6-oxo-3-pyridazinyl)phenyl]-(1H-imidazol-1)acetamide

A solution of 0.68 g of imidazole in 8 ml of dry DMF is added dropwise to a suspension of 0.58 g of NaOH (50%) in 8 ml of DMF under $N_2$. After the addition is over, the reaction mixture is stirred for an additional 30 minutes followed by the addition of 2.65 g of N-[4-1,4,5,6-tetrahydro-6-oxo-3-pyridazinyl)phenyl]-chloroacetamide in 10 ml of DMF. The reaction mixture is stirred overnight at room temperature and then poured into 100 ml of water. The precipitate is filtered, washed with water, and finally crystallized from DMF water to give 1.4 g of the product, N-[4-(1,4,5,6-tetrahydro-6-oxo-3-pyridazinyl)phenyl]-(1H-imidazole-1)acetamide as light brown powder, mp 260°–264° (darkens at 230° C.).

EXAMPLE 36

4,5-Dihydro-6-[4-(2-oxo-1-pyrrolidinyl)phenyl]-3(2H)-pyridazinone

A mixture of 2.3 g of 6-(4-aminophenyl)-4,5-dihydro-3(2H)-pyridazinone (prepared by following the procedure described in DT-2150685-0 patent), 1.9 g of 4-chlorobutyryl chloride in 25 ml of pyridine is stirred overnight at room temperature followed by heating for two hours. The pyridine is replaced by 20 ml of DMF, 0.2 g of NaOMe is added and the reaction mixture is heated on a steambath for five hours. The DMF is distilled under reduced pressure and the residue is treated with water. The pH of the solution is adjusted to 6, the solid is filtered and crystallized from a small volume of DMF to yield 0.9 g of the product, 4,5-dihydro-6-[4-(2-oxo-1-pyrrolidinyl)phenyl]-3(2H)-pyridazinone, mp 262°–263° C.

Anal. Calcd for $C_{14}H_{15}N_3O_2$, 0.2 DMF: C, 64.44; H, 6.03; N, 16.47. Found: C, 64.09; H, 5.95; N, 16.17.

EXAMPLE 37

4,5-Dihydro-6-[4-[1,4-dioxa-8-azaspiro[4,5]dec-8-yl]phenyl]-3(2H)-pyridazinone

A mixture of 19.6 g of 4-fluoro-γ-oxobenzenebutanoic acid [prepared by following the procedure of W. Adcock and M. J. S. Dewar, J. Amer. Chem. Soc., 89, 2(1967)], 14.3 g of 1,4-dioxa-8-azaspiro[4,5]decane and 13.9 g of anhydrous $K_2CO_3$ in 75 ml of DMSO is heated at 100° C. for 18 hours and cooled. The reaction mixture is filtered and the residue is washed with DMSO. The filtrate and the washings are diluted with 300 ml of water and the pH of the solution is adjusted to 6. The solid is filtered, washed with water, and air-dried to yield 15.0 g of 4-(1,4-dioxa-8-azaspiro [4,5]-dec-8-yl)-γ-oxobenzenebutanoic acid as off-white powder, mp 130°–131° C.

A mixture of 7.0 g of the above acid and 3.0 ml of 85% hydrazine hydrate in 70 ml of ethanol is heated to reflux for five hours and cooled. The solid is filtered and crystallized from methanol to yield 4.4 g of the product, 4,5-dihydro-6-[4-[1,4-dioxa-8-azaspiro-[4,5]dec-8-yl]phenyl]-3(2H)-pyridazinone (2a), mp 233°–234° C.

Anal. Calcd for $C_{17}H_{21}N_3O_3$: C, 64.74; H, 6.71; N, 13.33. Found: C, 64.52; H, 6.64; N, 13.33.

Similarly, 4,5-dihydro-6-[4-[1,4-dioxa-8-azaspiro[4,5]dec-8-yl]-phenyl-5-methyl-3(2H)-mp 234°–235° C. was obtained by following the procedure described in Example 38.

Following the procedure described in Example 38 but using a molar equivalent quantity of the appropriate 3- and 4-hydroxypiperidine in place of 1,4-dioxa-8-azaspiro[4,5]decane one obtains the suitably substituted γ-oxobenzenebutanoic acids which upon cyclization with hydrazine gives the following compounds: 37b. 4,5-dihydro-6-[4-(4-hydroxy-1-piperidinyl)phenyl]-3(2H)-pyridazinone, mp 262°–263° C. 37c. 4,5-Dihydro-6-[4-(3-hydroxy-1-piperdinyl)phenyl]-3(2H)-pyridazinone, mp 211°–212° C.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

TEST FOR IN VIVO MYOCARDIAL INTROPIC ACTIVITY IN ANESTHETIZED DOG

This screen consists of determining the effects of increasing intravenous doses of compound on mycardial contractility (dP/dt max of left ventricular blood pressure), heart rate, and aortic blood pressure of the pentobarbital-anesthetized dog.

METHODS

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Miller catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.01 to 0.31 mg/kg/min cause dose related significant increases in cardiac contractility with only low or minimal changes in heart rate and blood pressure.

| Example | Dose (mg/kg) | % Change Myocardial Contractility | Heart Rate | Blood Pressure |
|---|---|---|---|---|
| Test Results of 4,5-Dihydro-6-(1H—imidazol-1-yl)-phenyl]-3(2H)—pyridazinones Using Anesthetized Dog Procedure | | | | |
| 3a | 0.01 | 9 | −4.0 | −2.0 |
|    | 0.03 | 32 | −4.0 | −6.0 |
|    | 0.10 | 57 | −1.0 | −10.5 |
|    | 0.31 | 87 | 2.0 | −21.5 |
| 6  | 0.01 | 6 | −2.0 | 1.0 |
|    | 0.10 | 36 | −1.0 | −1.0 |
|    | 0.30 | 71 | 2.0 | −8.0 |
|    | 1.0  | 114 | 11.0 | −20.0 |
| 8  | 0.01 | 10 | −3.0 | −2.5 |
|    | 0.03 | 21 | −15.0 | −7.0 |
|    | 0.10 | 51 | −17.0 | −11.0 |
|    | 0.31 | 95 | −18.0 | −17.0 |
|    | 1.0  | 127 | −7.0 | −27.0 |
| Test Results of 6-(1H—Imidazol-1-yl)phenyl]-3(2H)—pyridazinone Using Anesthetized Dog Procedure | | | | |
| 13a | 0.01 | 3 | 0.0 | 0.0 |
|     | 0.03 | 15 | 6.0 | −1.5 |
|     | 0.10 | 40 | 16.0 | −6.0 |
|     | 0.31 | 78 | 32.0 | −9.0 |

The usefulness of the compounds of the present invention as antihypertensive agents is demonstrated by their effective in standard pharmacological test procedures, for example, in causing a significant decrease in mean arterial blood pressure in conscious rat. This test procedure is described in the following paragraphs.

A METHOD FOR THE DIRECT MONITORING OF AORTIC BLOOD PRESSURE AND HEART RATE FROM CONSCIOUS RAT

The continuous monitoring of pulsatile blood pressure from unrestrained conscious rats surgically equipped with polyethylene cannulas was accomplished by means of a computer assisted data capture scheme (CADCS). The basic elements of the methodology are the cannulation procedure and the CADCS.

METHOD

Cannulation Procedure:

Rats were anesthetized with Telazol (1:1 tiletamine HCl and zolazepam HCl; WL/PD, Ann Arbor, MI) 20–40 mg/kg IM and decending aorta exposed via a midline incision. Cannulus fabricated from polyethylene tubing (Clay Adams, Parsippany, NJ) were inserted into the aorta via an undersized puncture hole below the renal arteries. The puncture hole was made by a 23 g disposable needle with a section of the aorta clamped off above and below the puncture site. The cannulus, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scapulae (3-1 green braided suture; Deknatel, Queens Village, NY). The midline incision was closed in two steps (muscle first, skin second) using continuous over-and-over sutures 4-0 chronic; Ethicon, Somerville, NJ). Each rat was then given penicillin 30,000 units subcutaneously (Penicillin G Procaine Sterile Suspension; Parke-Davis, Detroit, MI).

The rats were fitted with a harness-spring-swivel assembly designed to protect the cannula and to provide the rat relative freedom of movement. The harnesses were fabricated from nylon hook and loop tape (Velcro, Manchester, NH) cemented to a metal plate to which spring wires (18-8 stainless steel, Paragon Spring; Chicago, IL) were attached to brass swivels (BRS/LVE, Bellville, MD). Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, MA) by means of PE100 tubing. While on test, each rat received a continuous slow infusion of heparinized saline solution (approximately 400 γ) or 40 units of heparin per 24-hour period) to prevent clot formation. Additional "flushes" of the cannula with heparinized saline were carried out when the aortic pulse pressure (systolic minus diastolic) was less than 25 mm Hg.

CADCS:

The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer (Varian V-74 or IBM). The overall scheme involved modulating the primary signal from the pressure transducer, generating the primary data set of the one-minute values for systolic, diastolic, and mean blood pressures and heart rate by the in-lab microcomputer and the storage, analysis, and report generation by the main research computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow lumened cannula. The distortion was 22-26 Hz and thus provided a reliable estimate of both systolic and diastolic blood pressure.

The microcomputers (one for each of two groups of 16 rats) were connected to the input components through the module interface units, an anlog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and and the marker switch status for each of the 32 stations were sampled every 10 msec. The microcomputer processed each blood pressure sample as it was received to produce "running average" values for heart rate, and mean, systolic and diastolic blood pressures.

When tested by the above procedure, the compounds of Formula I or pharmaceutically acceptable acid-addition salts thereof, e.g., Example 3(a-m), 6,8,9, 10,11,12 at doses 1, 3, 10, and 30 mg/kg were found to cause a significant reduction in aortic blood pressure.

When tested by the above procedure, the compounds of Formula I or pharmaceutically acceptable acid-addition salts thereof, e.g., Example 13 (a-i), 14,15, 16 at doses 1, 3, 10, and 30 mg/kg were found to cause a significant reduction in aortic blood pressure.

The actual determination of the numerical cardiotonic data definitive for any other particular compound of the invention is readily obtained according to the above-described standard test procedure by those skilled in pharmacological test procedures, without any need for any extensive experimentation.

The present invention includes within its scope a cardiotonic or antihypertensive composition for increasing cardiac contractility or lowering blood pressure, said composition comprising a pharmaceutically acceptable carrier and, as the active component thereof, a cardiotonic or antihypertensive compound of the present invention or pharmaceutically acceptable acid-addition salt thereof. The invention also includes within its scope the method for increasing cardiac contractility or lowering blood pressure in a patient requiring such treatment which comprises administering to such patient an effective amount of a compound of the present invention or pharmaceutically acceptable acid-addition salt thereof. In clinical practice, the said compounds of the present invention will normally be administered orally or parenterally in a wide variety of dosage forms.

Solid compositions for oral administration include compressed tablets, pills, powders, and granules. In such solid compositions, at least one inert diluent such as starch, calcium carbonate, sucrose, or lactose. These compositions may also contain additional substances other than inert dilutents, e.g., lubricating agents such as magnesium stearate, talc, and the like.

Liquid compositions for oral administration include pharmaceutically acceptable emulsions, solutions, suspensions, syrups, and elixirs containing inert diluents commonly used in the art, such as water or liquid paraffin. Besides inert diluents such compositions may also contain adjuvants, such as wetting and suspending agents, and sweetening, flavoring, and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous organic, and organic solutions, suspensions and emulsions. Examples or organic solvents or suspending media are propylene glycol, polethylene glycol, vegetable oils such as olive oil and injectable organic esters such as ethyl oleate. These compositions may also contain adjuvants such as stabilizing, preserving, wetting, emulsifying, and dispersing agents.

They may be sterilized, for example, by filtration through a bacteria-retaining filter, by incorporation of sterilizing agents in the compositions, by irradiation or by heating. They may also be manufactured in the form of sterile solid compositions which can be dissolved in sterile water or some sterile injectable medium immediately before use.

The percentage of active component in the said composition and method for increasing cardiac contractility may be varied so that a suitable dosage is obtained. The dosage administered to a particular patient is variable, depending upon the clinician's judgment using as the criteria: The route of administration, the duration of treatment, the size and condition of the patient, the potency of the active compound and the patient's response thereto. An effective dosage amount of active component can thus only be determined by the clinician considering all criteria and utilizing his best judgment on the patient's behalf.

We claim:

1. A compound of the formula

[structure]

wherein ==== represents a double or single bond between two carbon atoms; Q is oxygen or sulfur; $R_2$ is hydrogen or lower alkyl; $R_3$ is hydrogen, lower alkyl, or when ==== represents a single bond, $R_3$ is di-lower alkyl; $R_4$ is hydrogen, lower alkyl or when ==== represents a double bond, $R_4$ is hydrogen, lower alkyl amino, cyano, $CONR_aR_b$, hydroxy, $CH_2OH$ or $$\overset{(O)_n}{\underset{}{\overset{\|}{S}}}-R_c,$$

where $R_a$ and $R_b$ are independently H or lower alkyl, $R_c$ is lower alkyl or phenyl, and n is zero to two; or $R_3$ and $R_4$ taken together form a ring containing one to four carbon atoms; Y is H, halogen, lower alkyl, lower alkoxy, or a group such as $$OCH_2\underset{OH}{\overset{|}{C}H}CH_2NR_dR_e$$

where $R_d$ and $R_e$ are independently H, lower alkyl, $(CH_2)_nR_f$ where $R_f$ is a benzene ring optionally substituted by halogen, hydroxy, lower alkyl, lower alkoxy, and $CF_3$, and n is zero to three, and A is any of the groups from a-e, and is attached to the 3- or 4-position of the phenyl ring:

a.

[structure]

wherein $R_1$, R', and R are independently hydrogen or lower alkyl, $CH_2OH$, $SCH_3$, $SOCH_3$, $SO_2CH_3$, hydroxyalkyl, halogen, $(CH_2)_kNR''$, R''', wherein k is zero to two and $R_2$ and $R_3$ are independently hydrogen or lower alkyl, wherein lower alkyl contains one to six carbon atoms; X is a bond, or $O(CH_2)_n$ wherein n is two to five; with the proviso that when (i) X is a bond and is attached to the 4-position of the phenyl ring and (ii) Y is H, the groups $R_1$, R', and R cannot be H or lower alkyl;

b.

[structure]

where
(i) W=L=Z=CH
(ii) W=Z=N and L=CH or
(iii) L=Z=N and W=CH
and X is a bond, $(CH_2)_n$ or $O(CH_2)_{n+1}$ wherein n is one to four;

c.

[structure] (i)

$$A = (CH_2)_n\text{-ring with C=O and N-X}$$

wherein n is one to three; or

[structure] (ii)

wherein $R_8$ and $R_9$ is ethylenedioxy and the pharmaceutically acceptable acid addition salts thereof; X is the same as defined in 1b, or d.

[structure]

wherein ==== represents a double or single bond between two carbon atoms; $R_{11}$ is hydrogen or lower alkyl; M is NH, O, or S, and X is a direct bond or

[structure]

where X, M, and $R_{11}$ are the same as defined above, and the pharmaceutically acceptable acid addition salts thereof.

2. A compound according to claim 1 having the structure:

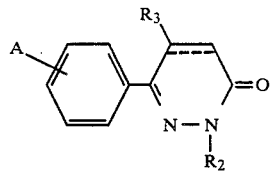

where A, R$_2$, and R$_3$ are the same as defined in claim 1(a-d).

3. A compound according to claim 1 having the structure:

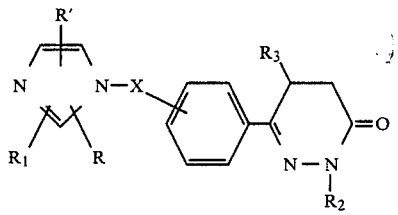

wherein R$_1$, R', X, R$_2$, and R$_3$ are as defined in claim 1a, and pharmaceutically acceptable acid addition salts thereof.

4. A compound according to claim 1 having the structure:

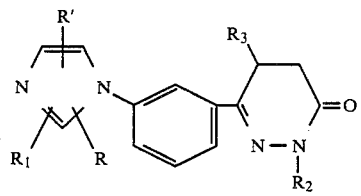

wherein R$_1$, R', R, R$_2$, and R$_3$ are as defined in claim 1a, and the pharmaceutically acceptable acid addition salts thereof.

5. A compound according to claim 1 having the structure:

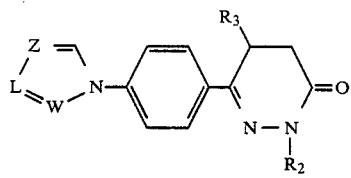

wherein W, L, Z, R$_2$, and R$_3$ are as defined in claim 1b, and the pharmaceutically acceptable acid addition salts thereof.

6. A compound according to claim 1 having the structure:

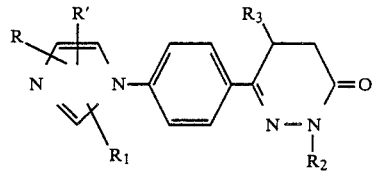

wherein R$_1$, R, R', R$_2$, and R$_3$ are as defined in claim 1a, and the pharmaceutically acceptable acid addition salts thereof.

7. A compound according to claim 2 having the structure:

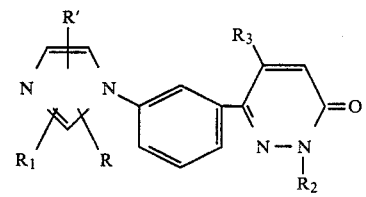

wherein R$_1$, R', R, R$_2$, and R$_3$ are as defined in claim 2, and the pharmaceutically acceptable acid addition salts thereof.

8. A compound according to claim 2 having the structure:

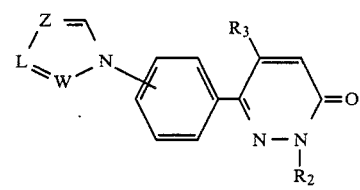

wherein W, L, Z, R$_2$, and R$_3$ are as defined in claim 2, and the pharmaceutically acceptable acid addition salts thereof.

9. A compound according to claim 2 having the structure:

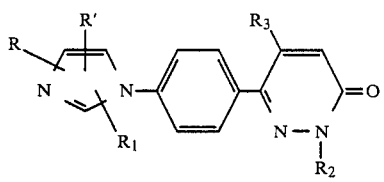

wherein R$_1$, R, R', R$_2$, and R$_3$ are as defined in claim 2, and the pharmaceutically acceptable acid addition salts thereof.

10. A compound according to claim 1 having the structure:

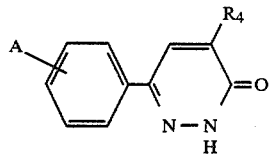

wherein R$_4$ and A are as defined in claim 1a and b, and the pharmaceutically acceptable acid addition salts thereof.

11. A compound according to claim 10 wherein A is imidazole or imidazole substituted by lower alkyl, S-lower alkyl or CH$_2$OH, tetrahydrobenzimidazole, benzimidazole, or 1,2,4-triazole, and the pharmaceutically acceptable acid addition salts.

12. A compound according to claim 1, wherein R$_3$ and R$_4$ are as defined in claim 1 and A is as defined in claim 1c.

13. A compound according to claim 12 having the structure:

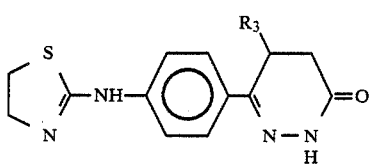

wherein R$_3$ is hydrogen or lower alkyl and the pharmaceutically acceptable acid addition salts thereof.

14. A compound according to claim 4, which is 4,5-dihydro-6-[3-(1H-imidazol-1-yl)phenyl]-3(2H)-pyridazinone.

15. A compound according to claim 5 which is 4,5-dihydro-6-[4-(1H-1,2,4-triazol-1-yl)phenyl]-3(2H)-pyridazinone.

16. A compound which is 4,5-dihydro-6-[4-(1H-benzimidazol-1-yl)phenyl]-3(2H)-pyridazinone.

17. A compound according to claim 6, which is 4,5-dihydro-6-[4-(4-hydroxymethyl-1H-imidazol-1-yl)phenyl]-3(2H)-pyridazinone.

18. A compound according to claim 6, which is 4,5-dihydro-6-[4-(2-methylthio-1H-imidazol-1-yl)-phenyl]-3(2H)-pyridazinone.

19. A compound according to claim 6, which is 4,5-dihydro-6-[4-(2-methylsulfinyl-1H-imidazol-1-yl)phenyl]-3(2H)-pyridazinone.

20. A compound according to claim 6, which is 4,5-dihydro-6-[4-(2-methylsulfonyl-1H-imidazol-1-yl)phenyl]-3(2H)-pyridazinone.

21. A compound according to claim 7, which is 6-[3-(1H-imidazol-1-yl)phenyl]-3(2H)-pyridazinone.

22. A compound according to claim 8, which is 6-[4-(1H-1,2,4-triazol-1-yl)phenyl]-3(2H)-pyridazinone.

23. A compound according to claim 9, which is 6-[4-(4-hydroxymethyl-1H-imidazol-1-yl)phenyl]-3(2H)-pyridazinone.

24. A compound according to claim 9, which is 6-[4-(2-methylthio-1H-imidazol-1-yl)phenyl]-3(2H)-pyridazinone.

25. A compound according to claim 9, which is 6-[4-(2-methylsulfinyl-1H-imidazol-1-yl)phenyl]-3(2H)-pyridazinone.

26. A compound according to claim 9, which is 6-[4-(2-methylsulfonyl-1H-imidazol-1-yl)phenyl]-3(2H)-pyridazinone.

27. A compound which is 6-[4-(1H-benzimidazol-1-yl)phenyl]-3(2H)-pyridazinone.

28. A compound according to claim 9, which is 6-[4-[(4,5-dihydro-2-thiazolyl)amino]phenyl]-4,5-dihydro-3(2H)-pyridazinone.

29. A compound according to claim 10, which is 4-amino-6-[4-(1H)-imidazol-1-yl)-phenyl]-3(2H)-pyridazinone.

30. A compound according to claim 13, which is 4,5-dihydro-6-[4-[1,4-dioxa-8-azaspiro[4,5]dec-8-yl]phenyl]-3(2H)-pyridazinone.

31. A compound according to claim 13, which is 4,5-dihydro-6-[4-[1,4-dioxa-8-azaspiro[4,5]dec-8-yl]phenyl]-5-methyl-3(2H)-pyridazinone.

32. A compound according to claim 10, which is 2,3-dihydro-6-[4-(1H-imidazol-1-yl)phenyl]-3-oxo-4-pyridazine carbonitrile.

33. A pharmaceutical composition for increasing cardiac contractility comprising an effective amount of a compound as claimed in claim 1 with a pharmaceutically acceptable carrier.

34. The method for increasing cardiac contractility in a patient requiring such treatment comprising administering orally or parenterally to such patients an effective amount of a compound of the Formula I

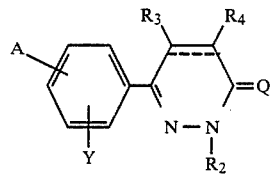

wherein ===== represents a double or single bond between two carbon atoms; R$_2$ is hydrogen or lower alkyl; R$_3$ is hydrogen, lower alkyl, or when ===== represents a single bond, R$_3$ is di-lower alkyl; Q is oxygen or sulfur, R$_4$ is hydrogen, lower alkyl or when ===== represents a double bond, R$_4$ is hydrogen, lower alkyl, amino, cyano, CONR$_a$R$_b$,

where R$_a$ and R$_b$ are independently H or lower alkyl, R$_c$ is lower alkyl or phenyl, and n is zero to two; or R$_3$ and R$_4$ taken together form a ring containing one to four carbon atoms; Y is H, halogen, lower alkyl, lower alkoxy, or a group such as

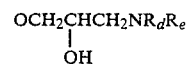

where R$_d$ and R$_e$ are independently H, lower alkyl, (CH$_2$)$_n$R$_f$ where R$_f$ is a benzene ring optionally substituted by halogen, hydroxy, lower alkyl, lower alkoxy, and CF$_3$ and n is zero to three, and A is any of the groups from a-e, and is attached to the 3- or 4-position of the phenyl ring:

a.

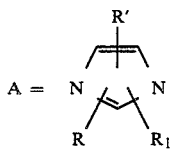

wherein R$_1$, R', and R are independently hydrogen or lower alkyl, CH$_2$OH, SCH$_3$, SOCH$_3$, SO$_2$CH$_3$, hydroxyalkyl, halogen, (CH$_2$)$_k$NR'', R''', wherein k is zero to two and R$_2$ and R$_3$ are independently hydrogen or lower alkyl, wherein lower alkyl contains one to six carbon atoms; or, when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkyloxy, and (iii) pyridine ring; X is a bond, (CH$_2$)$_n$ or O(CH$_2$)$_{n+1}$ wherein n is one to four; with the proviso that when (i) X is a bond and is attached to the 4-position of the phenyl ring and (ii) Y is H, the groups R$_1$, R', and R cannot be H or lower alkyl;

b.

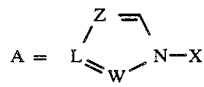

wherein
(i) W=L=X=CH
(ii) W=Z=N and L=CH or
(iii) L=Z=N and W=CH
and X is the same as defined in 1a.

c.

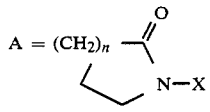 (i)

wherein n is one to three; or

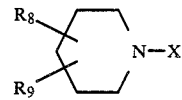 (ii)

wherein R$_8$ is hydrogen and R$_8$ and R$_9$ are independently lower alkyl, phenyl, hydroxy, lower alkoxy, NHR$_{17}$ where R$_{17}$ is hydrogen, lower alkyl or lower alkanoyl, CO$_2$R$_{18}$ where R$_{18}$ is hydrogen or lower alkyl OCOB R$_{10}$ where R$_{10}$ is alkyl phenyl, or pyridyl and B is a direct bond or NH; or taken together are carbonyl or ethylenedioxy and the pharmaceutically acceptable acid addition salts thereof; X is the same as defined in 1a;

d.

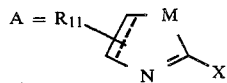

wherein ----- represents a double or single bond between two carbon atoms; R$_{11}$ is hydrogen or lower alkyl; M is NH, O, or S, and X is either a direct bond or NH; or

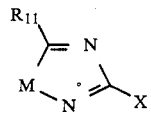

where X, M, and R$_{11}$ are the same as defined above, and the pharmaceutically acceptable acid addition salts thereof.

* * * * *